United States Patent [19]

Etes

[11] 4,054,140
[45] Oct. 18, 1977

[54] OSTOMY APPLIANCE
[75] Inventor: Donald E. Etes, Crystal Lake, Ill.
[73] Assignee: Donald E. Etes, Crystal Lake, Ill.
[21] Appl. No.: 600,845
[22] Filed: July 31, 1975
[51] Int. Cl.² ............................................. A61F 5/44
[52] U.S. Cl. ................................................... 128/283
[58] Field of Search ......... 128/283, 294, 295, DIG. 24

[56] References Cited

U.S. PATENT DOCUMENTS

| 2,496,175 | 1/1950 | Perry | 128/283 |
|---|---|---|---|
| 2,639,710 | 5/1953 | Fario | 128/283 |
| 2,784,718 | 3/1957 | Fenton | 178/283 |
| 2,818,069 | 12/1957 | Fenton | 128/283 |
| 2,928,393 | 3/1960 | Marsan | 128/283 |
| 3,439,679 | 4/1969 | Doolittle | 128/283 |
| 3,481,336 | 12/1969 | Ipson | 128/283 |
| 3,495,592 | 2/1970 | Herman | 128/283 |
| 3,528,420 | 9/1970 | Nielsen | 128/283 |
| 3,789,846 | 2/1974 | Barrett | 128/283 |
| 3,827,435 | 8/1974 | Marsan | 128/283 |
| 3,897,781 | 8/1975 | Marsan | 128/283 |

FOREIGN PATENT DOCUMENTS

| 1,105,558 | 4/1961 | Germany | 128/283 |
|---|---|---|---|

Primary Examiner—J. Reed Fisher
Attorney, Agent, or Firm—Emrich, Root, O'Keeffe, & Lee

[57] ABSTRACT

An ostomy appliance for mounting around the stoma opening of a patient and embodying a receptacle of the disposable or throw-away type for receiving drainage from the stoma of a patient, with the receptacle being readily removable, but effectively mounted on a supporting member which is readily attachable to a patient's body, and the appliance embodying novel pad structure which is effective to protect a stoma, or the like, from injury, and which is also effective to afford a seal between the appliance and the patient's body for preventing or reducing seepage from the stoma opening onto the skin of the patient.

1 Claim, 4 Drawing Figures

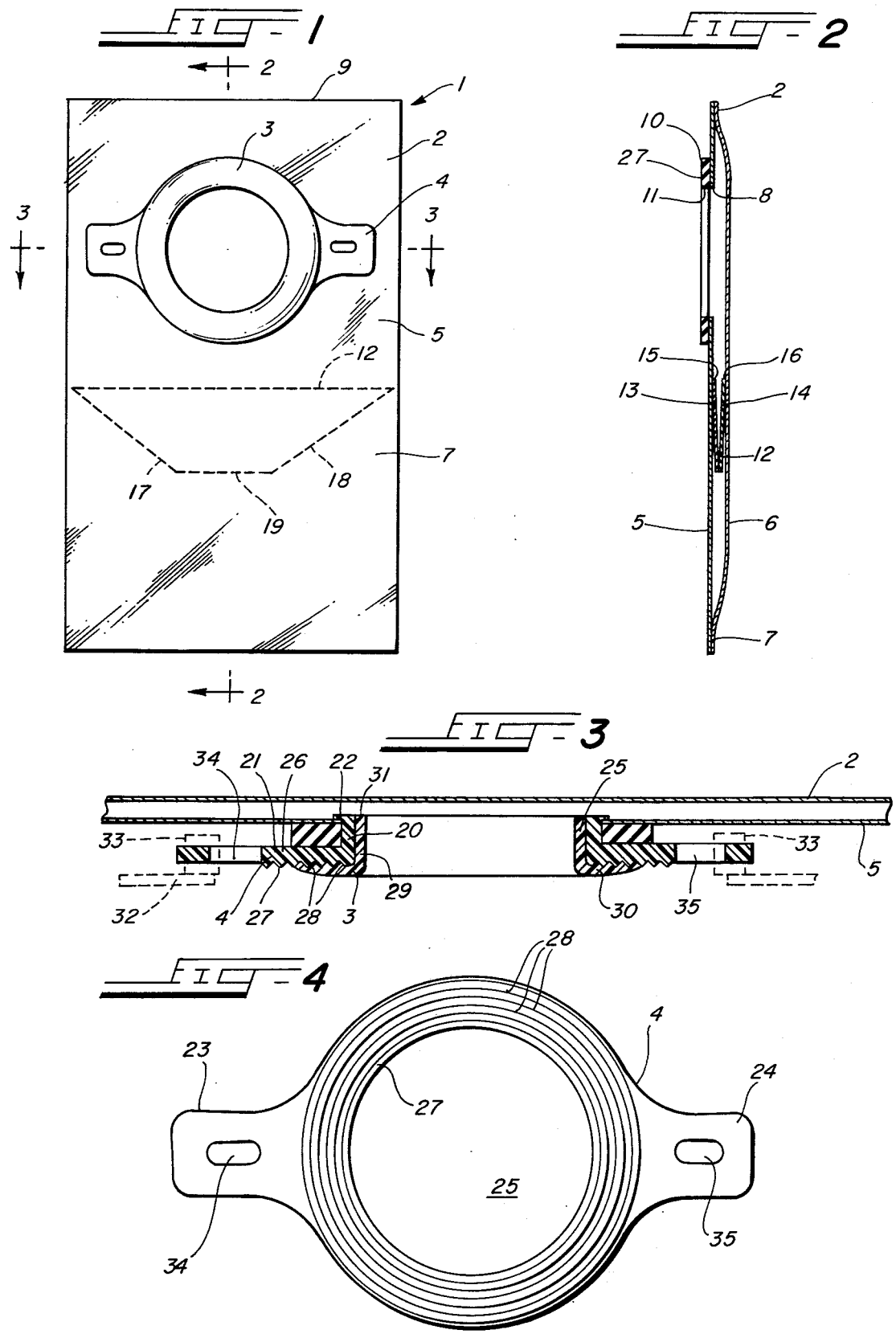

OSTOMY APPLIANCE

BACKGROUND OF THE INVENTION

The present invention relates to medical appliances, and, more particularly, to medical appliances which are particularly well adapted for use as ostomy appliances.

It is a primary object of the present invention to afford a novel medical appliance which is particularly well adapted for use around a stoma opening in a patient for receiving drainage from the stoma of such a patient.

Ostomy appliances of the nature to which the present invention generally relates have been heretofore known in the art, being shown, for example, in United States Letters Patent such as Gricks U.S. Pat. No. 1,922,763 issued Aug. 15, 1933; Perry U.S. Pat. No. 2,648,675, issued July 27, 1954; Tezak U.S. Pat. No. 3,040,745, issued June 26, 1962; Kanter U.S. Pat. No. 3,366,114, issued Jan. 30, 1968; and Nielson U.S. Pat. No. 3,528,420, issued Sept. 15, 1970.

Ostomy appliances of such a nature, heretofore known in the art, have had several inherent disadvantages, such as, for example, being uncomfortable for the patient to wear; failing to protect portions of the patient's body, and, in some instances, actually causing injury to the same; causing irritation to the skin of the patient; not being effective to prevent the seepage of fluids and other matter from the stoma opening, or the like, of a patient onto the skin of the patient; not being effectively held in proper position on a patient; not being readily removable and replaceable; being complicated in construction and operation; or being difficult and expensive to manufacture, and the like. It is an important object of the present invention to overcome such disadvantages.

Another object of the present invention is to afford a novel ostomy appliance which is highly effective to prevent or reduce seepage from a stoma opening onto the skin of a patient.

Another object of the present invention is to afford a novel ostomy appliance for mounting around the stoma opening of a patient for receiving stoma drainage, and which appliance is so constructed that effective protection is afforded against injury to the stoma.

Yet another object of the present invention is to afford a novel ostomy appliance which embodies disposable patient-engaging pad portions and disposable drainage-receiving receptacle portions, which portions are constituted and arranged in a novel and expeditious manner.

A further object of the present invention is to afford a novel ostomy appliance which may be quickly and easily removed from, and replaced on the body of a patient.

An object ancillary to the foregoing is to enable such removal and replacement to be quickly and easily effected without causing damage or irritation to the body of the patient.

Another object of the present invention is to afford a novel ostomy appliance which is practical and efficient in operation, and which may be readily and economically produced commercially.

Other and further objects of the present invention will be apparent from the following description and claims and are illustrated in the accompanying drawings which, by way of illustration, show the preferred embodiment of the present invention and the principles thereof and what I now consider to be the best mode in which I have contemplated applying these principles. Other embodiments of the invention embodying the same or equivalent principles may be used and structural changes may be made as desired by those skilled in the art without departing from the present invention and the purview of the appended claims.

SUMMARY OF THE INVENTION

A medical appliance which is particularly well adapted for mounting around the stoma opening of a patient, with the appliance embodying a reinforced, disposable receptable and a disposable patient-engaging pad mounted on a supporting unit, and with the receptacle and pad being quickly and easily removable and replaceable relative to the supporting unit and relative to each other. The entire combination of parts of the appliance affords an assembly which effectively protects the body of a patient wearing the same from injury, while affording an assembly wherein the individual parts, which are the most susceptible to being contaminated or to deterioration, may be quickly and easily removed and replaced by unskilled persons.

DESCRIPTION OF THE DRAWINGS

In the drawings:

FIG. 1 is a front elevational view of an ostomy appliance embodying the principles of the present invention;

FIG. 2 is a longitudinal sectional view taken substantially along the line 2—2 in FIG. 1;

FIG. 3 is a transverse sectional view taken substantially along the line 3—3 in FIG. 1; and FIG. 4 is a front elevational view of the face plate shown in FIGS. 1 and 3.

DESCRIPTION OF THE EMBODIMENT SHOWN HEREIN

An ostomy appliance 1 is shown in the drawings to illustrate the presently preferred embodiment of the present invention.

The appliance 1 embodies, in general, a receptacle in the form of a bag 2 having a pad in the form of a sealing ring 3 and a supporting plate 4 removably mounted on one wall 5 of the bag 2, FIGS. 1 and 3.

The receptacle 2, preferably, is in the form of a flexible, substantially rectangular-shaped bag made of a suitable water-impervious material such as, for example, polyethylene or polypropylene. However, as will be appreciated by those skilled in the art a suitable receptacle other than the aforementioned bag may be utilized without departing from the purview of the broader aspects of the present invention.

The bag 2 shown in the drawings embodies the aforementioned wall 5 and an oppositely disposed wall 6. The walls 5 and 6 preferably are substantially rectangular in shape and are secured to each other around their outer peripheral edges 7 by suitable means, such as, for example, heat sealing.

A substantially round opening 8 extends through the wall 5 in downwardly spaced, but relatively closely adjacent relation to the top edge 9 of the bag 2, FIG. 2, and an annular reinforcing member 10 is disposed on the outer face of the wall 5 in surrounding relation to the opening 8. The reinforcing member 10 preferably is in the form of a resilient ring made from a suitable adhesive material, such as, for example, the material disclosed in my co-pending application for U.S. Patent, Ser. No. 600,847, filed July 1, 1975, and is adhesively secured to the outer face of the wall 5 so as to afford, with the bag 2, a disposable or throw-away item. The opening 11 in the pad 10 preferably is of the same size and shape as the opening 8 in the bag 2, and is disposed in axial alignment therewith.

In the preferred form of the ostomy appliance 1 shown in the drawings, a valve 12 is disposed in the bag 2 below the opening 8 for a purpose which will be discussed in greater detail presently. The valve 12 embodies two sheets 13 and 14 of suitable material, such as, for example, the aforementioned polyethylene or polypropylene, secured at their upper edges 15 and 16, respectively, to the inner faces of the walls 5 and 6, respectively, of the bag 2 by suitable means, such as, for example, the aforementioned heat sealing. The sheets 13 and 14 are disposed in parallel relation to each other, and each embodies two oppositely disposed side edges 17 and 18, FIG. 1, sloping downwardly and inwardly from the respective upper edges 15 and 16 to a bottom edge 19. The sheets 13 and 14 are secured together along their edges 17 and 18 by suitable means, such as, for example, the aforementioned heat sealing, from the upper edges 15 and 16 thereof to the lower edges 19. The lower edges 19 are left unsecured relative to each other.

With this construction, the valve 12 affords a substantially funnel-shaped member through which material, such as liquid, or the like, may relatively readily pass downwardly therethrough, into the lower portion of the bag 2, but which affords a restriction, which is highly effective to prevent reverse flow of such matter upwardly through the valve 12. The supporting plate or face plate 4 of the ostomy appliance 2 embodies a tubular body portion 20 having two radially outwardly projecting flanges 21 and 22 disposed at the opposite ends thereof, FIG. 3. The tubular body portion 20 preferably is round in transverse cross section and is of uniform inside and outside diameter throughout its length. The flange 21 is of substantially greater outside diameter than the flange 22, and has two ears 23 and 24 projecting outwardly from diametrically, oppositely disposed portions thereof for a purpose which will be discussed in greater detail presently.

In the assembled ostomy appliance 1, the tubular portion 20 of the supporting plate 4 is disposed in the openings 11 and 8 in the pad 10 and the bag 2, respectively, with the axially extending opening 25 through the tubular body portion 20 disposed in axial alignment with the openings 11 and 8. In such assembled relation of the supporting plate 4 to the bag 2, the flange 22 is disposed in abutting engagement with the inner face of the wall 5 of the bag 2, around the opening 8, and the flange 21 is disposed in abutting engagement with the outer face of the pad 10, the spacing between the flanges 21 and 22 preferably being such that the pad 10 is clampingly engaged therebetween with a relatively snug, but freely removable fit.

The pad 10 preferably is substantially flat, and, likewise, the face 26 of the flange 21, which engages the face 27 of the pad 10, remote from the bag 2, in the assembled ostomy appliance 1, preferably is flat. The face 27, remote from the face 26, of the flange 21 has a plurality of outwardly projecting ribs 28 thereon, for a purpose which will be discussed in greater detail presently, the ribs 28 being in the form of a plurality of spaced, concentric circles disposed concentrically around the opening 25 through the tubular body portion 20.

The pad or sealing ring 3 embodies a central tubular portion 20 having a radially outwardly projecting flange 30 at one end thereof. The central tubular portion 29, like the tubular body portion 20 of the supporting plate 4, preferably is round in transverse cross section and is of uniform inside and outside diameters throughout its length.

In the assembled ostomy appliance 1, the pad 3 is mounted on the supporting plate 4 with the central tubular portion 29 disposed in the tubular body portion 20 of the supporting plate 4 with a relatively snug, but freely slidable fit; and with the flange 30 disposed in overlying juxtaposition to the ribs 28 on the face 27 of the flange 21 of the supporting plate 4, FIG. 3. The central tubular portion 29 of the pad 3 preferably is of such length that when the pad 3 is disposed in the aforementioned assembly relation to the supporting plate 4, the end 31 thereof, remote from the flange 30, is disposed in uniplanar relation to the face of the flange 22 of the supporting plate 4 remote from the flange 21 thereof, as illustrated in FIG. 3.

The pad 3, like the pad 10 may be made of any suitable material, but, preferably, is made of a suitable resilient adhesive material such as the material disclosed in my aforementioned U.S. patent application, Ser. No. 600,847.

In the use of my novel ostomy appliance 1, with the appliance 1 assembled in the manner illustrated in FIG. 3, it is placed on the body of an ostomy patient with the opening 25 through the pad 3 disposed in axial alignment with the stoma opening in the patient, and with the flange 30 of the pad 3 disposed in snugly abutting engagement with that portion of the skin of the patient immediately surrounding the stoma opening. Preferably, the opening 25 through the pad 3 is of such size that when the appliance 1 is disposed in operative position on the patient, the stoma of the patient is received therein with a relatively loose, slidable fit, so as to protect against constriction of the stoma by the appliance 1. Preferably, the pad 3 is constructed of such material, or has a coating on the face of the flange 30, remote from the supporting plate 4, of such a nature that it is adhesively, but readily removably secured to the skin of the patient.

In the use of the ostomy appliance 1, after it has been disposed in the aforementioned manner of the body of the patient, it may be additionally secured by suitable means, such as, for example, an elastic belt 32, having suitable fastening members, such as hooks 33, at the opposite ends thereof releasably secured in openings 34 and 35 in the ears 23 and 24, respectively, of the supporting plate 4, as illustrated somewhat diagramatically in broken lines in FIG. 3.

With the ostomy appliance 1 constructed in the manner disclosed herein, it affords an appliance wherein the pad 3 and the assembly afforded by the receptacle 2 and the pad 10 may be quickly, easily and selectively replaced relative to the supporting plate 4. It will be remembered that the pad 3 is preferably made of a material such as is disclosed in my aforementioned U.S. patent application, Ser. No. 600,847, which is protective and adhesive in nature. Even when such materials are used in the construction of the pad 3, the construction of the face 27 of the flange 21 of the supporting plate 4 is such that when it is desired to remove the pad 3 from the supporting plate 4, the flange 30 may be relatively easily peeled off from the face 27 of the flange 21 by reason of the intermittent adherence of the flange 30 to the face 27 because of the ribs 28. Such adherence is sufficiently strong to prevent slippage or other movement between the flanges 21 and 30 during use of the ostomy appliance 1, but is sufficiently weakened because of the novel ribbed construction of the face 27 that even relatively strongly adhering materials may be readily peeled therefrom when it is desired to remove them from the supporting plate 4.

With the appliance 1 constructed in the aforementioned manner, it will be seen that the pad 3 affords effective protection against possibly injurious engagement of a stoma, extending therethrough, with the supporting plate 4 and the portion of the bag wall 5 surrounding the opening 8.

From the foregoing it will be seen that the present invention affords a novel ostomy appliance.

In addition, it will be seen that the present invention affords a novel ostomy appliance wherein the receptacle portion thereof may be of a readily removable and disposable type, and wherein the sealing ring or resilient pad portion thereof, which is engaged with the skin of the patient around the stoma opening, and which is subject to deterioration or contamination, or both, may be quickly and easily removed and replaced.

In addition, it will be seen that the present invention affords a novel ostomy appliance which is practical and efficient in operation, and which may be readily and economically produced commercially.

Thus, while I have illustrated and described the preferred embodiment of my invention, it is to be understood that this is capable of variation and modification, and I therefore do not wish to be limited to the precise details set forth, but desire to avail myself of such changes and alterations as fall within the purview of the following claims.

I claim:

1. An ostomy appliance for mounting on the body of a patient in position for receiving drainage from the stoma of the patient, said appliance comprising
   a. a receptacle for receiving such drainage,
   b. said receptacle having
      1. top and bottom edges, and
      2. an opening through one wall thereof in downwardly spaced relation to said top edge, for receiving the stoma of such a patient therein,
   c. resilient, annular reinforcing means
      1. permanently secured to the outer face of said wall in axially aligned surrounding relation to said opening and
      2. projecting laterally outwardly away from said outer face,
   d. a supporting plate having
      1. a tubular body portion, and
      2. two flanges projecting radially outwardly from respective opposite ends of said body portion,
   e. said supporting plate being removably mounted on said receptacle with
      1. said body portion disposed in axial alignment with said opening, and
      2. said reinforcing means clampingly disposed between said two flanges, and
   f. said reinforcing means comprising a substantially flat, uniplanar pad adhesively secured to said receptacle in position wherein the substantially flat sides of said pad coact with respective ones of said flanges so as to be clamped therebetween,
   g. a resilient pad having
      1. a central tubular portion, and
      2. an annular flange projecting radially outwardly from one end of said central tubular portion,
   h. said resilient pad being removably mounted on said supporting plate with
      1. said central tubular portion extending into said tubular body portion, and
      2. said annular flange disposed in outwardly overlying juxtaposition to the outer face of the one of said two flanges remote from said receptacle,
   i. said last mentioned flange including means for connection to opposite ends of a supporting band.

* * * * *